United States Patent [19]
Bourgeois et al.

[11] Patent Number: 5,492,021
[45] Date of Patent: Feb. 20, 1996

[54] VARIABLE DEPTH CORE SAMPLER

[75] Inventors: Peter M. Bourgeois, Hamburg; Robert J. Reger, Grand Island, both of N.Y.

[73] Assignee: The United States of America as represented by the United States Department of Energy, Washington, D.C.

[21] Appl. No.: 312,740

[22] Filed: Sep. 27, 1994

[51] Int. Cl.⁶ .................................................... G01N 1/04
[52] U.S. Cl. ........................................ 73/864.45; 83/919
[58] Field of Search .......................... 73/864.44, 864.45; 83/919; 30/174, 278, 301, 316, 352; 175/249, 248, 253, 403, 404; 99/538; 408/67, 204–207

[56] References Cited

U.S. PATENT DOCUMENTS

4,779,689 10/1988 Paxton, III ............................... 175/403
4,785,826 11/1988 Ward .......................................... 30/174
4,946,000 8/1990 Gibson et al. ............................ 175/403

Primary Examiner—Robert Raevis
Attorney, Agent, or Firm—Tim Harney; Hugh Glenn; William R. Moser

[57] ABSTRACT

A variable depth core sampler apparatus comprising a first circular hole saw member, having longitudinal sections that collapses to form a point and capture a sample, and a second circular hole saw member residing inside said first hole saw member to support the longitudinal sections of said first hole saw member and prevent them from collapsing to form a point. The second hole saw member may be raised and lowered inside said first hole saw member.

15 Claims, 7 Drawing Sheets

VARIABLE DEPTH CORE SAMPLER

CONTRACTUAL ORIGIN OF THE INVENTION

The U.S. Government has rights in this invention under Contract No. DE-AC07-81NE44139 between the U.S. Department of Energy and West Valley Nuclear Service.

BACKGROUND OF THE INVENTION

This invention relates to a sampling means, more particularly to a device to sample hard surfaces at varying depths.

Often it is desirable to take samples of a hard surface wherein the samples are of the same diameter but of varying depths. Current practice requires that a full top-to-bottom sample of the material be taken, using a hole saw, and boring a hole from one end of the material to the other. The sample thus taken is removed from the hole saw and the middle of said sample is then subjected to further investigation. Such sampling devices are well known, as described in U.S. Pat. No. 4,741,651 issued May 3, 1988, No. 5,076,741 issued Dec. 31, 1991 and No. 5,061,176 issued Oct. 29, 1988. Other similar sampling devices are set forth in U.S. Pat. No. 3,596,719 issued Aug. 3, 1971, No. 4,779,689 issued Oct. 25, 1988 and No. 5,289,727 issued Mar. 1, 1994.

The prior art set forth above requires either only soft material be sampled or a top-to-bottom sample be taken of the entire material.

It is therefore an object of the present invention to provide a sampling device which, not only provides a uniform sample of a hard material, but also provides such sampling at variable depths of such hard material.

Another object of this invention is to provide a sampling device, and a method of taking samples, that is simple and inexpensive to manufacture and use.

Additional objects, advantages and novel features of this invention will become apparent to those skilled in the art upon examination of the following and by practice of the invention.

SUMMARY OF THE INVENTION

One embodiment of the invention comprises a variable depth core sampler having a cylindrical hole saw member with an open end, a closed end and a wall extending between the two ends. The wall of the hole saw member has a plurality of longitudinal sections, with a weakened portion at the base of each section, that are separated by a plurality of longitudinal slots in communication with and extending from the open cutting end part way along the length of the wall. This arrangement permits the longitudinal sections to collapse at the weakened portions to form a point and capture a sample. The variable depth core sampler also has rotational force supplied to it, preferably by means of a mandrel attached to the closed end, and a spacer apparatus to prevent the longitudinal sections from collapsing. In this embodiment, the spacer apparatus comprises a spacer ring that resides inside the holesaw member and is in supporting contact with the longitudinal sections, preventing the longitudinal sections from collapsing to form a point until a sample is taken. This spacer ring slides lengthwise between its first location at the open cutting and its second location located beyond the base of the longitudinal sections. When the spacer ring has slide to the second location, lateral support to the longitudinal sections is removed permitting the sections to collapse to form a point and capture a sample.

Another embodiment of the invention comprises a variable depth core sampler apparatus with a first cylindrical hole saw member as described above. In this embodiment, the spacer apparatus includes a second cylindrical hole saw member having a second open cutting end, a second closed end and a wall extending between the two ends, residing inside the first hole saw member and in supporting contact with the longitudinal sections of the first hole saw member, preventing the sections from collapsing to form a point and capture a sample. The connection between the two hole saw members includes an L-shaped opening in the first hole saw member with a pin fixably attached to the second hole saw member slidably engaging the L-shaped opening. This arrangement could also include two or more L-shaped holes and two or more pins fixably attached to the wall of the second hole member slidably engaging the L-shaped holes. In this instance, the operator of the sampler determines the desired depth of the sample by manually rotating the pin(s). The second hole saw is now free to move vertically with respect to the first hole saw and recede or slide back into the first hole saw. When the second hole saw has passed the end of the slots, the weakened area causes the sections to collapse to form a point, in the process biting off a sample of material.

The foregoing arrangements provides a means for sampling a hard material at a predetermined depth.

BRIEF DESCRIPTIONS OF THE DRAWINGS

The present invention is illustrated in the accompanying drawings wherein.

DETAILED DESCRIPTION OF THE INVENTION

Figure 1:
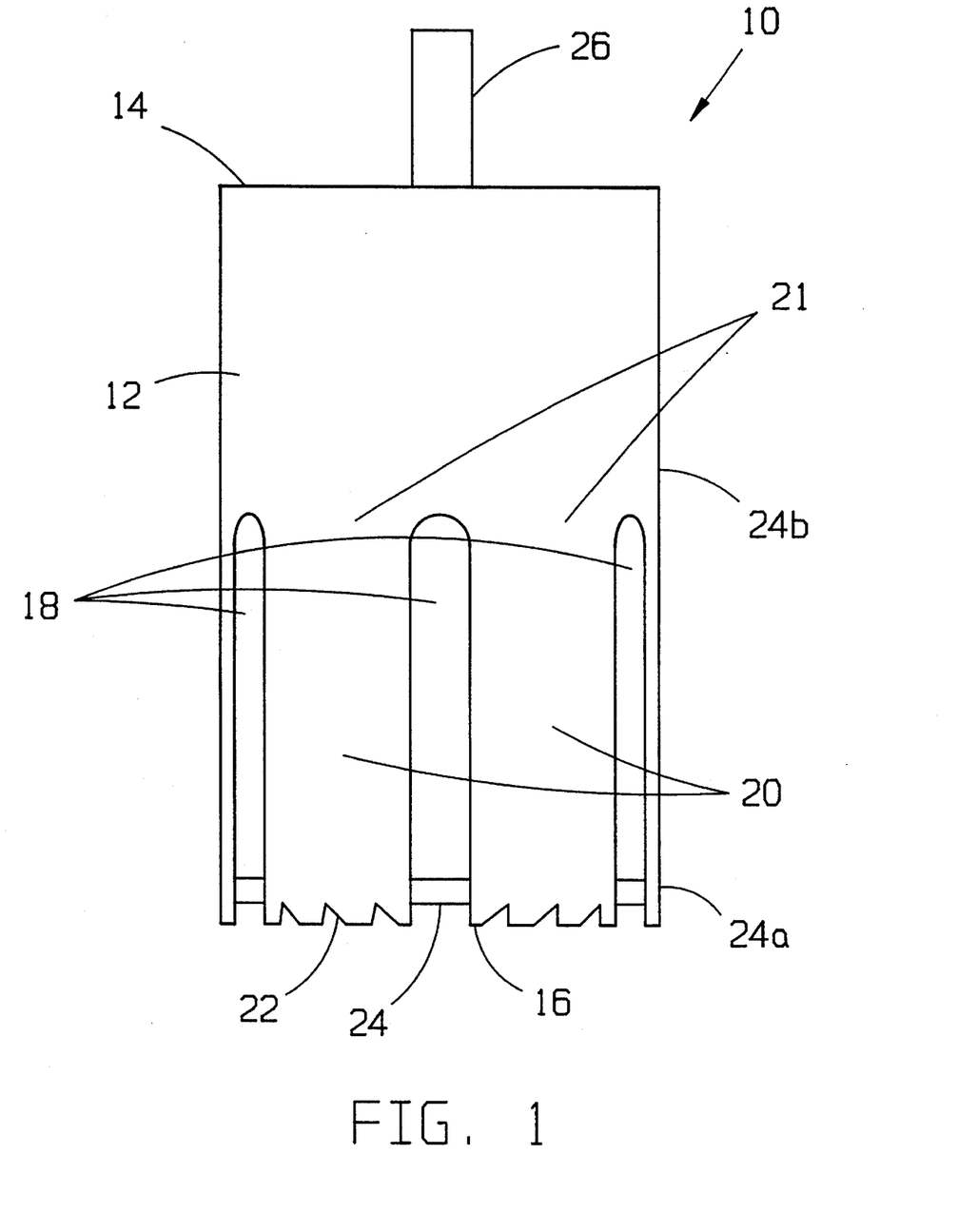
FIG. 1 is an elevation view of a variable depth core sampler with longitudinal sections illustrated in an uncollapsed mode.
Figure 2:
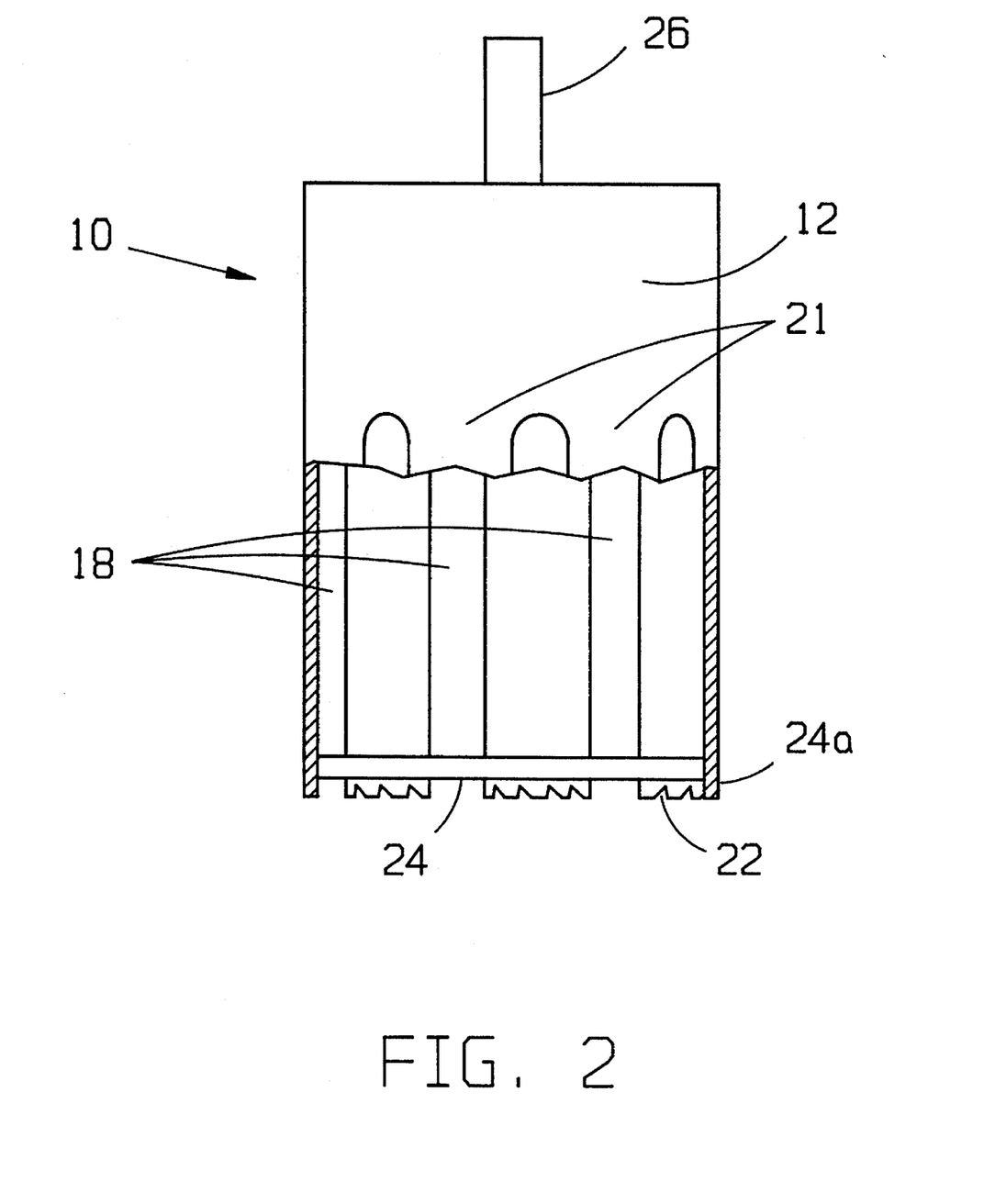
FIG. 2 is a partially cut away view of the variable depth core sampler of FIG. 1, illustrating an internal spacer ring in a first location.
Figure 3:
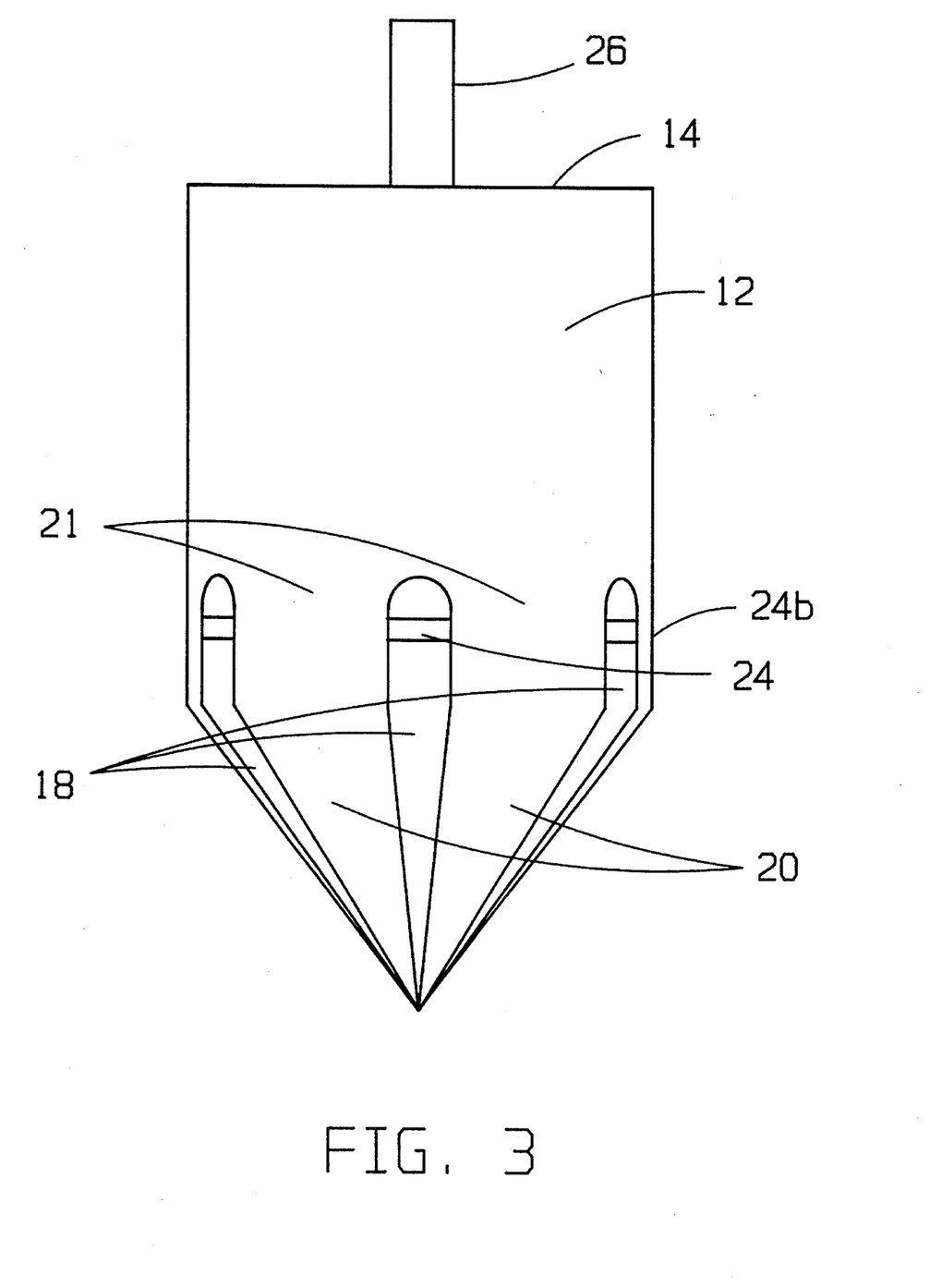
FIG. 3 is an elevation view of the variable depth core sampler of FIG. 1 wherein the spacer ring is in a second location with the longitudinal sections collapsed to form a point.

One embodiment of the rotating variable depth core sampler apparatus is illustrated in FIGS. 1,2 and 3. FIG. 1 illustrates circular hole saw 10 having a closed end 14 and peripheral, cylindrical wall 12 extending from closed end 14, forming open cutting end 16. Open cutting end 16 has cutting teeth 22 along its peripheral edge. Mandrel 26 is attached to closed end 14 and is mounted in a motor or chuck of a drill (not shown) to provide rotation to hole saw apparatus 10. Wall 12 has a plurality of longitudinal slots 18 in communication with and extending from open cutting end 16, preferably of equal length. The length of longitudinal slots 18 is dependant on the length of the sample to be taken. In addition, wall 12 has longitudinal sections 20 extending from open cutting end 16 with weakened portions 21 at the base of longitudinal sections 20. Spacer ring 24 resides inside hole saw 10, in contact with and supporting said longitudinal sections 20.

In one manner of forming the variable depth core sampler, a plurality of longitudinal slots 18 are cut part way along the length of peripheral, cylindrical wall 12. The length of slots 18 is determined by the depth of the sample to be taken, i.e., shorter slots result in a short or shallow sample, while longer slots result in a long or more substantial sample. The remaining longitudinal sections 20 are bent to form a point, as depicted in FIG. 3. This produces weakened proximal portions 21 at the base of each longitudinal section 20 to encourage bending once spacer ring 24 is displaced. Longitudinal sections 20 are pried apart and spacer ring 24 is inserted into hole saw 10, as set forth in FIG. 2, supporting said longitudinal sections 20 to prevent them from collapsing to form a point until a sample is taken. Spacer ring 24 resides lengthwise inside hole saw 10 at first location 24a at open cutting end 16, in supporting contact with longitudinal sections 20.

Mandrel 26 is mounted in motor or chuck of a drill (not shown) and rotation is transmitted to hole saw 10 by means of mandrel 26. Hole saw 10 is then sawed into the material to be sampled in the usual manner. As hole saw 10 moves through the material to be sampled, the sample core forces spacer ring 24 to slide back into hole saw 10. When spacer ring 24 has receded or slid past the base of longitudinal slots 18 to second location 24b, longitudinal sections 20 collapse upon themselves by bending at weakened portions 21, as depicted in FIG. 2, biting off a sample of the material in the process. A carrot shaped sample is then found inside the body of hole saw 10.

Figure 4:
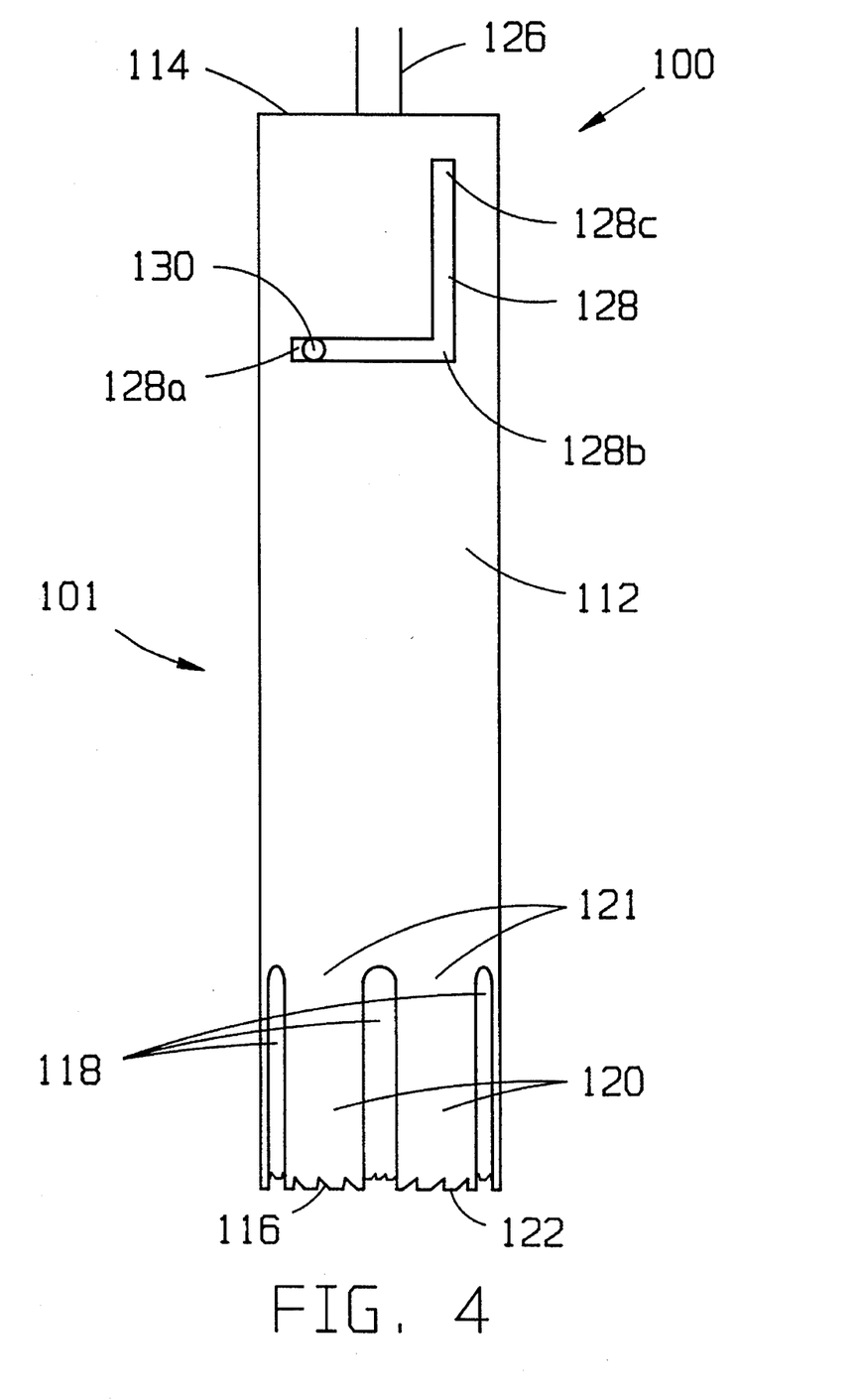
FIG. 4 is an elevation view of a second embodiment of the variable depth core sampler with longitudinal sections of a first hole saw member illustrated in an uncollapsed mode.

Another embodiment of the rotating variable depth core sampler 100 is illustrated in FIGS. 4,5,6 and 7. FIG. 4 illustrates first hole saw member 101 having first closed end 114 and peripheral, cylindrical wall 112 extending from first closed end 114 forming first open cutting end 116, with cutting teeth 122 along its peripheral edge, and mandrel 126 connected to closed end 114. Wall 112 has a plurality of longitudinal slots 118 in communication with and extending from open cutting end 116, preferably of equal length. Longitudinal slots 118 form longitudinal sections 120 extending from open cutting end 116, having weakened proximal portions 121 at the base of each longitudinal sections 120. In addition, wall 112 has an L-shaped opening 128, having positions 128a, 128b and 128c. Preferably, wall 112 would have two or more such L-shaped openings 128.

Figure 5:
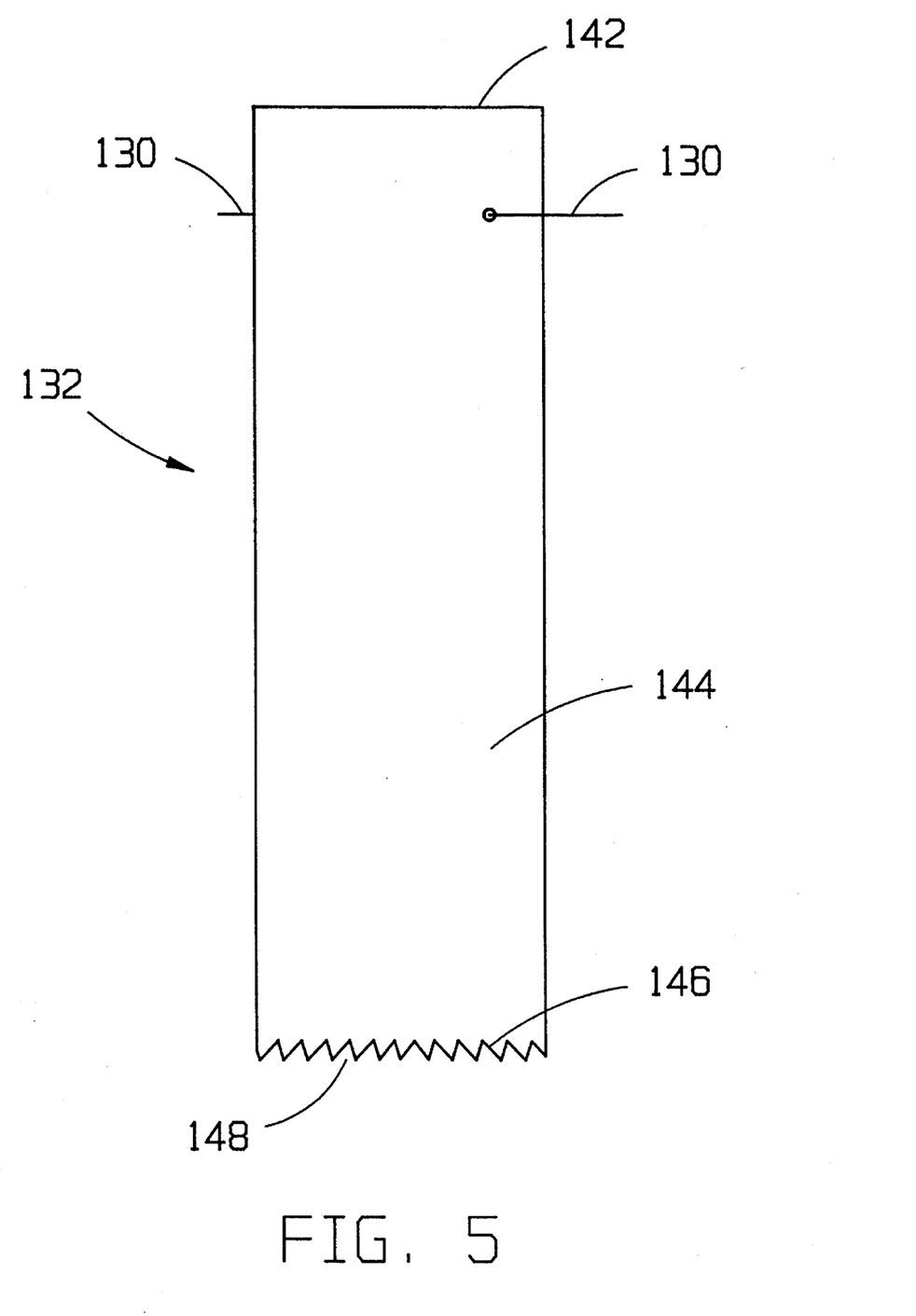
FIG. 5 is an elevation view of a second hole saw member inside the variable depth core sampler of FIG. 4.
Figure 6:
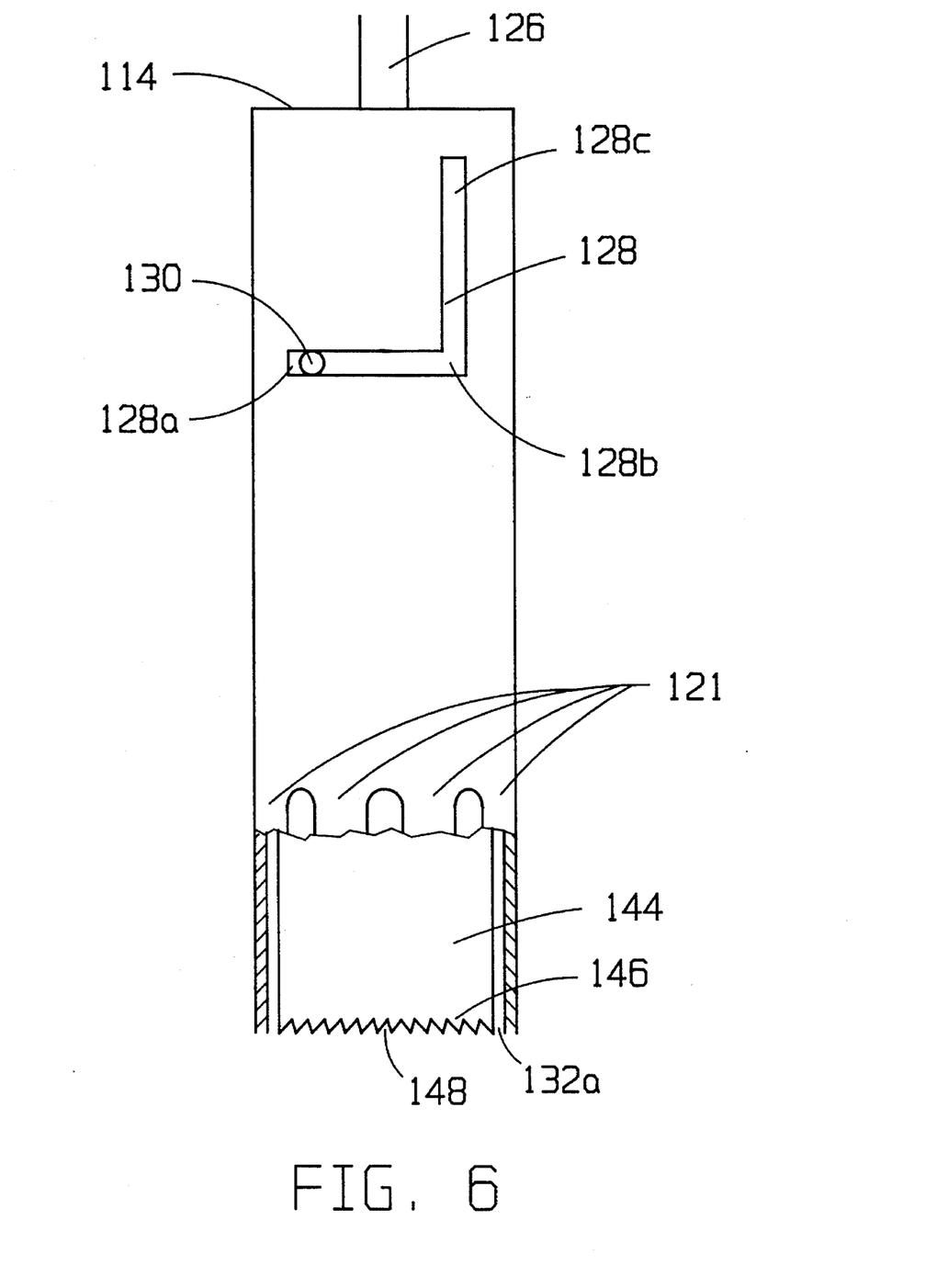
FIG. 6 is a partially cut away view of the variable depth core sampler of FIG. 4 illustrating the second hole saw member of FIG. 5 in place.

A second hole saw member 132, having second closed end 142 and peripheral, cylindrical wall 144 extending from second closed end 142 forming second open cutting end 146, with cutting teeth 148 along its peripheral edge, depicted in FIG. 5, resides in first hole saw member 101, as demonstrated in FIG. 6. Second hole saw member 132 is in contact with and supports said longitudinal sections 120 and prevents them from collapsing to form a point until a sample is taken. Second hole saw member 132 is coupled to first hole saw member 101 by means of pin 130 fixably attached to wall 144 opposing each other, illustrated in FIG. 5, that slidably engage L-shaped opening 128, as shown in FIGS. 4 & 6.

Figure 7:
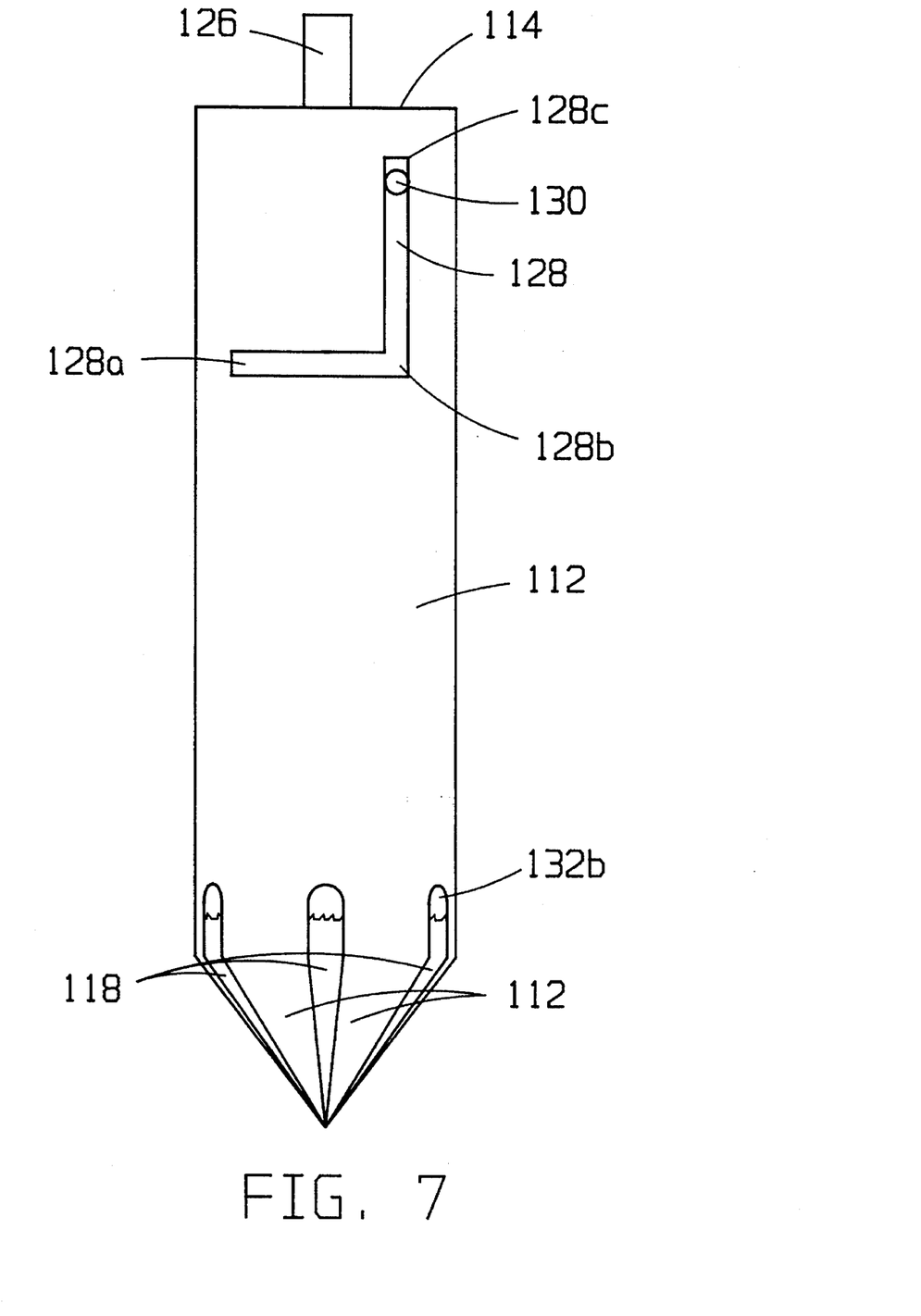
FIG. 7 is an elevation view of the second embodiment of the variable depth core sampler of FIG. 4 with the longitudinal sections of the first hole saw member collapsed to form a point.

In a second manner of forming a variable depth core sampler, a plurality of longitudinal slots 118 are cut part way along the length of peripheral, cylindrical wall 112 forming longitudinal sections 120, and an L-shaped opening is cut into wall 112. Longitudinal sections 120 are bent to form a point as illustrated in FIG. 7. This produces weakened portions 121 at the base of each longitudinal section 120 to encourage bending. Said longitudinal sections 120 are pried apart and second hole saw member 132 is inserted in hole saw member 101, as depicted in FIG. 6. Second hole saw member 132 is in contact with and supports longitudinal sections 120 and prevents them from collapsing to form a point until a sample is taken. Second hole saw member 132 is coupled to first hole saw member 101 by means of a pin 130 fixably attached to wall 144 protruding through and slidably engaging L-shaped opening 128, as illustrated in FIGS. 4 & 6. Preferably, the second hole saw member 132 is coupled to the first hole saw member 101 by means of two or more pins 130 slidably engaging two or more L-shaped openings.

Mandrel 126 is mounted in a motor or chuck of a drill (not shown) and rotation is transmitted to first hole saw member 101. The sampler is then sawed into the material to be sampled in the usual manner. When pin 130 is in position 128a, second hole saw member 132 is in first location 132a, preventing longitudinal sections 120 from collapsing. Pin 130 is held in position 128a, and consequentially second hole saw member 132 is kept in first location 132a, by means of the rotational force exerted by first hole saw member 101 against pin 130. When first hole saw member 101 reaches the desired depth of the material to be sampled, as determined by the operator, pin 130 is manually moved from position 128a to position 128b, subsequently rotating second hole saw member 132 inside first hole saw member 101. Pin 130 is now free to move vertically to position 128c, causing second hole saw member 132 to move vertically with respect to first hole saw member 101. When second hole saw member moves to second location 132b inside first hole saw member 101, longitudinal sections 120 collapse to form a point, as illustrated in FIG. 7, biting off a sample in the process. A carrot shaped sample is then found inside the body of hole saw member 132.

The embodiment of this invention in which an exclusive property or privilege is claimed is defined as follows:

1. A variable depth core sampler apparatus comprising:
   a cylindrical hole saw member having an open cutting end, a closed end, a cylindrical wall extending lengthwise therebetween and a plurality of longitudinal slots communicating with said open cutting end part way along the length of said cylindrical wall, forming a plurality of longitudinal sections separated thereby, and permitting the longitudinal sections to collapse to form a point and capture a sample;
   means for rotating said hole saw member around its longitudinal axis; and
   means for preventing said longitudinal sections from collapsing.

2. The variable depth core sampler of claim 1 wherein said open cutting end further comprises a plurality of cutting teeth along the peripheral edge thereof.

3. The variable depth core sampler of claim 1 wherein said rotating means further comprises a mandrel connected to said closed end.

4. The variable depth core sampler of claim 1 wherein the length of said longitudinal slots are selected to correspond to the length of the sample to be taken.

5. The variable depth core sampler of claim 1 wherein the prevention means further comprises a spacer ring residing inside and in supporting contact with said longitudinal sections, whereby said longitudinal sections are prevented from collapsing to form a point.

6. The variable depth core sampler of claim 5 wherein said spacer ring is in slidable contact lengthwise between a first location in supporting contact with said longitudinal sections and a second location lengthwise beyond said longitudinal sections whereby lateral support is removed permitting said longitudinal sections to collapse to form a point and capture a sample.

7. The variable depth core sampler of claim 6 wherein said longitudinal sections have a weakened proximal portion at which said longitudinal sections bend and thereby collapse to form a point.

8. A variable depth core sampler apparatus comprising:

a first cylindrical hole saw member having a first open cutting end, a first closed end, a cylindrical wall extending lengthwise therebetween, and a plurality of longitudinal slots communicating with and extending part way along the length of said wall, forming a plurality of longitudinal sections separated thereby, and permitting the longitudinal sections to collapse to form a point and capture a sample;

means for rotating said first hole saw member around its longitudinal axis;

a second cylindrical hole saw member having a second open cutting end, a second closed end and a cylindrical wall extending therebetween, residing inside and in supporting contact with the longitudinal sections of said first hole saw member, whereby said longitudinal sections are prevented from collapsing to form a point; and means for movably connecting said second hole saw member to said first hole saw member.

9. The variable depth core sampler of claim 8 wherein the first open cutting end further comprises a plurality of cutting teeth along the peripheral edge thereof.

10. The variable depth core sampler of claim 8 wherein the second open cutting end further comprises a plurality of cutting teeth along the peripheral edge thereof.

11. The variable depth core sampler of claim 8 wherein the rotating means further comprises a mandrel connected to the first closed end of said first hole saw member.

12. The variable depth core sampler of claim 8 wherein said longitudinal sections have a weakened proximal portion at which said longitudinal sections bend and thereby collapse to form a point.

13. The variable depth core sampler of claim 8 wherein the moveable connection means further comprises an L-shaped opening in the wall of said first hole saw member and a pin fixably attached to the wall of said second hole saw member slidably engaging said L-shaped opening, whereby said second hole saw member moved vertically with respect to said first hole saw member, permitting the longitudinal sections of said first hole saw member to collapse to form a point.

14. The variable depth core sampler of claim 8 wherein the moveable connection means further comprises a plurality of L-shaped openings in the wall of said first hole saw member and a plurality of pins fixably attached to the wall of said second hole saw member slidably engaging said L-shaped openings, whereby said second hole saw member may be moved vertically with respect to said first hole saw member, permitting the longitudinal sections of said first hole saw member to collapse to form a point.

15. A variable depth core sampler apparatus comprising:

a first circular hole saw member having a first open cutting end with a plurality of cutting teeth along the peripheral edge thereof, a first closed end, a cylindrical wall extending therebetween and having an L-shaped opening in the wall of said first hole saw member and a plurality of longitudinal slots communicating with and extending from said first open cutting end part way along the length of said cylindrical wall forming a plurality of longitudinal sections separated thereby, wherein said longitudinal sections having a weakened proximal portion, permitting the remaining longitudinal sections to collapse to form a point and capture a sample;

a mandrel rotating said first hole saw member around its longitudinal axis;

a second circular hole saw member having an second open cutting end with a plurality of cutting teeth along the peripheral edge thereof, a second closed end and a cylindrical wall extending therebetween, residing inside and in supporting contact with the longitudinal sections of said first hole saw member, whereby said longitudinal sections are prevented from collapsing upon themselves; and a pin fixably attached to wall of said second hole saw member slidably engaging the L-shaped opening of said first hole saw member, whereby said second hole saw member may be moved vertically with respect to said first hole saw member.

* * * * *